US009717396B2

(12) United States Patent
Jungbauer et al.

(10) Patent No.: US 9,717,396 B2
(45) Date of Patent: Aug. 1, 2017

(54) VIDEO ENDOSCOPE WITH SIDEWAYS VIEWING DIRECTION AND METHOD FOR MOUNTING A VIDEO ENDOSCOPE

(71) Applicant: OLYMPUS WINTER & IBE GMBH, Hamburg (DE)

(72) Inventors: Sebastian Jungbauer, Hamburg (DE); Sebastian Stuehle, Hamburg (DE); Patrick Scherr, Alt-Moelln (DE); Ronny Huebl, Ellerhoop (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 336 days.

(21) Appl. No.: 14/299,264

(22) Filed: Jun. 9, 2014

(65) Prior Publication Data

US 2014/0288370 A1    Sep. 25, 2014

Related U.S. Application Data

(63) Continuation of application No. PCT/EP2012/005023, filed on Dec. 6, 2012.

(30) Foreign Application Priority Data

Dec. 20, 2011   (DE) .................. 10 2011 089 157

(51) Int. Cl.
*A61B 1/00* (2006.01)
*A61B 1/04* (2006.01)
*A61B 1/05* (2006.01)

(52) U.S. Cl.
CPC ...... *A61B 1/00135* (2013.01); *A61B 1/00096* (2013.01); *A61B 1/00101* (2013.01);
(Continued)

(58) Field of Classification Search
CPC ............ A61B 1/00096; A61B 1/00101; A61B 1/00105; A61B 1/00135; A61B 1/00177;
(Continued)

(56) References Cited

U.S. PATENT DOCUMENTS 5,538,497 A * 7/1996 Hori ................... A61B 1/00096
385/117
5,621,830 A   4/1997 Lucey et al.
(Continued)

FOREIGN PATENT DOCUMENTS

DE   102004023866 B3   2/2006
DE   102010044786 A1   3/2012
(Continued)

OTHER PUBLICATIONS

International Search Report dated Mar. 15, 2013 issued in PCT/EP2012/005023.
English Abstract of WO 2012/031644 dated Mar. 15, 2012.

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

A video endoscope with sideways viewing direction including an endoscope shaft having a jacket tube, an entry window joined hermetically to the jacket tube at the distal end of the jacket tube, a sideways viewing optical subassembly and a sensor module having an optical sensor, wherein the sensor module is disposed on a distal side of a longitudinally extended sensor module carrier that is rotatably mounted with respect to the jacket tube. In the video endoscope, the sideways viewing optical subassembly can be formed as an attachment which can be plugged distally onto the sensor module and/or the sensor module carrier and which is rotatably mounted with respect to the sensor module and/or the sensor module carrier, wherein the attach-
(Continued)

ment has at least one lock which interacts with at least one corresponding lock on the jacket tube, such that the attachment is rotationally fixed with respect to the jacket tube.

10 Claims, 2 Drawing Sheets

(52) U.S. Cl.
CPC ...... *A61B 1/00105* (2013.01); *A61B 1/00177* (2013.01); *A61B 1/00179* (2013.01); *A61B 1/053* (2013.01)

(58) Field of Classification Search
CPC ....... A61B 1/00179; A61B 1/053; A61B 1/05; H04N 2005/2255; H04N 5/2254; H04N 5/2252; H04N 5/2257; G02B 23/2484; G02B 23/2476; G02B 23/2423; G02B 23/2407
USPC ......................................................... 600/112
See application file for complete search history.

(56) References Cited

U.S. PATENT DOCUMENTS

| | | | | |
|---|---|---|---|---|
| 5,833,596 | A * | 11/1998 | Bonnell | A61B 1/042 250/353 |
| 5,961,445 | A * | 10/1999 | Chikama | A61B 1/00096 600/112 |
| 6,361,491 | B1 | 3/2002 | Hasegawa et al. | |
| 6,537,209 | B1 * | 3/2003 | Pinkhasik | A61B 1/00096 356/241.5 |
| 7,627,208 | B2 * | 12/2009 | Kuroiwa | A61B 5/0066 385/31 |
| 7,896,803 | B2 * | 3/2011 | Schara | A61B 1/00177 600/130 |
| 8,449,452 | B2 * | 5/2013 | Iddan | A61B 1/00158 600/109 |
| 2002/0028986 | A1 * | 3/2002 | Thompson | A61B 1/0669 600/178 |
| 2003/0092966 | A1 | 5/2003 | Schara et al. | |
| 2005/0143624 | A1 * | 6/2005 | Iddan | A61B 1/00094 600/112 |
| 2006/0183977 | A1 | 8/2006 | Ishigami et al. | |
| 2006/0206006 | A1 * | 9/2006 | Schara | A61B 1/00177 600/173 |
| 2007/0100202 | A1 | 5/2007 | Murata | |
| 2008/0108869 | A1 * | 5/2008 | Sanders | A61B 1/00105 600/109 |
| 2008/0214892 | A1 * | 9/2008 | Irion | A61B 1/05 600/112 |
| 2008/0300456 | A1 | 12/2008 | Irion et al. | |
| 2009/0112061 | A1 * | 4/2009 | Kim | A61B 1/00177 600/109 |
| 2009/0256914 | A1 * | 10/2009 | Silverman | G03B 17/02 348/157 |
| 2010/0188493 | A1 | 7/2010 | Kanzaki et al. | |
| 2014/0330082 | A1 * | 11/2014 | Navok | A61B 1/0011 600/176 |
| 2016/0256041 | A1 * | 9/2016 | Blanquart | H01L 27/14601 |

FOREIGN PATENT DOCUMENTS

| | | |
|---|---|---|
| DE | 102011076077 A1 | 11/2012 |
| EP | 1683472 A1 | 7/2006 |
| EP | 1997421 A1 | 12/2008 |

\* cited by examiner

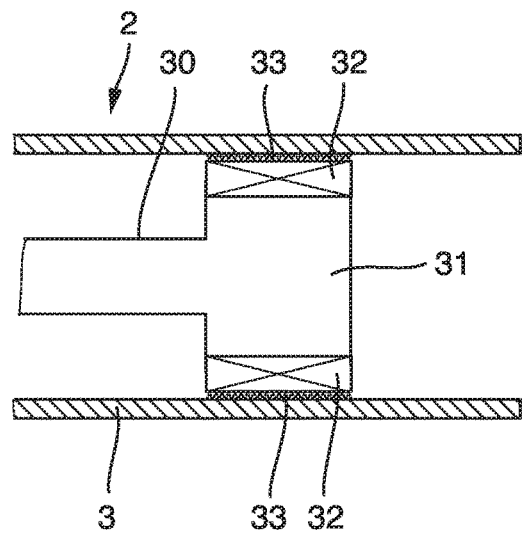
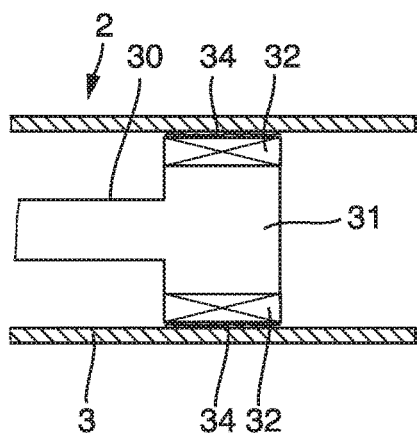
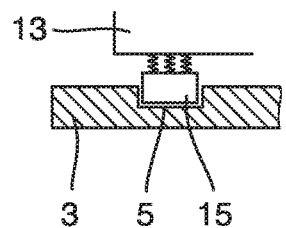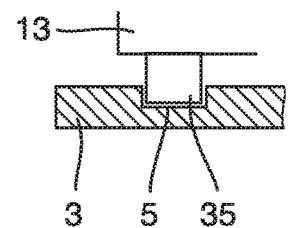

VIDEO ENDOSCOPE WITH SIDEWAYS VIEWING DIRECTION AND METHOD FOR MOUNTING A VIDEO ENDOSCOPE

CROSS-REFERENCE TO RELATED APPLICATION

The present application is a continuation of PCT/EP2012/005023 filed on Dec. 6, 2012, which is based upon and claims the benefit to DE 10 2011 089 157.9 filed on Dec. 20, 2011, the entire contents of each of which are incorporated herein by reference.

BACKGROUND

Field

The invention relates to a video endoscope with sideways viewing direction, and in particular to a video endoscope comprising an endoscope shaft having a jacket tube, an entry window joined hermetically to the jacket tube at the distal end of the jacket tube, in particular disposed obliquely with respect to the longitudinal axis of the jacket tube, and a sideways viewing optical subassembly and a sensor module having an optical sensor, wherein the sensor module is disposed on a distal side of a longitudinally extended sensor module carrier that is rotatably mounted with respect to the jacket tube. The invention further relates to a method for mounting a corresponding video endoscope.

Prior Art

Video endoscopes with a sideways viewing direction are used in order to inspect the area of certain organs as a result of the reduced space available in the anatomic space or respectively in the operative field in the case of endoscopic surgeries. During the use of these types of endoscopes it is customary that an endoscope rotatable in the longitudinal axis is made available to the user. In order to thereby accord the user or respectively operator the greatest possible comfort, a system is integrated into the endoscope in some cases, which makes it possible to retain the orientation of the image sensor and thus of the image during the rotation of the endoscope around its longitudinal axis. It is thus easier for the operator to keep his/her orientation in the operative field.

In order to ensure the autoclavability of such endoscopes, the movable optical components must be arranged in a hermetically sealed space. This is necessary in order to prevent the penetration of moisture into the optical system. The hermetically sealed space or respectively the hermetically sealed volume that extends from the endoscope tip up to the gripping area of the optics, comprises all optical components.

The requirement of a hermetical seal of the endoscope shaft in order to enable good autoclavability is usually ensured in that the entry window on the distal tip of the endoscope, which can be an inclined, in particular planar, entry window or for example a glass dome, which is designed in particular in a hemispherical shape, is connected circumferentially with the endoscope shaft, in particular a jacket tube of the endoscope shaft. A hermetic connection is for example established through soldering. The soldering takes place after the mounting of the subassemblies brought into the endoscope shaft. In this case, this can thus lead to impurities in the glass, mainly on the inside. In this kind of system, these impurities cannot be removed retroactively.

Another possibility for establishing a hermetic seal is the subsequent joining of the entire endoscope tip. Due to the potential deformation during the joining due to the heat input in the case of the specified tolerances of the optical subassemblies, this is very complex and correspondingly expensive.

SUMMARY

In contrast to this state of the art, the object of the present invention is to provide video endoscopes and a method for mounting video endoscopes, with which a video endoscope can be produced quickly and cleanly as well as within the specified tolerances, wherein an autoclavability of the video endoscope is ensured.

This object is solved through a video endoscope with sideways viewing direction, comprising an endoscope shaft having a jacket tube, an entry window joined hermetically to the jacket tube at the distal end of the jacket tube, in particular disposed obliquely with respect to a longitudinal axis of the jacket tube, a sideways viewing optical subassembly and a sensor module having an optical sensor, wherein the sensor module is disposed on a distal side of a longitudinally extended sensor module carrier that is rotatably mounted with respect to the jacket tube, in that the sideways viewing optical subassembly is designed as an attachment, which can be or is plugged distally onto the sensor module and/or the sensor module carrier and which is rotatably mounted with respect to the sensor module and/or the sensor module carrier, wherein the attachment has at least one locking means which interacts with at least one corresponding locking means on the jacket tube such that the attachment is rotationally fixed with respect to the jacket tube.

The invention is based on the use of an attachment. The attachment, which may also be called an extension, includes a prism or a mirror on a prism holder or a mirror holder and can be clipped on or mounted on the sensor module or the sensor module carrier. The attachment is rotatably mounted, for example using a slide bearing. For the first time, it is thereby possible to combine the components needing to be installed in the jacket tube and push them altogether as slide-in group into the jacket tube. This makes it possible to establish the hermetic seal of the jacket tube with the entry window for example through soldering and to subsequently clean for example the entry window also from the inside in the still empty jacket tube before the sensor module is pushed in with the prism holder or mirror holder.

Since, in the case of sideways viewing video endoscopes, the viewing direction and thus the orientation of the prism or mirror in the jacket tube are also important, the attachment also comprises a locking means, which works together with a corresponding locking means in the jacket tube so that a twisting of the prism or mirror in the attachment with respect to the jacket tube is prevented after being pushed in. The prism or respectively the mirror itself is moved via the locking means in the jacket tube and the rigid connection to the handle. The sensor module with the optical sensor is rotatably mounted with respect to the jacket tube and is also rotatably mounted with respect to the prism or mirror. These rotations are transferred for example from a proximally arranged means of rotation, for example an actuator or a magnetic coupling, via the sensor module carrier to the sensor module.

Within the framework of the present invention, the tube that is called a jacket tube is connected in a rotationally fixed manner with the prism or respectively the mirror, while the sensor module is rotatably mounted with respect to the jacket tube. In alternative variants, the jacket tube designed in this manner can also be an inner tube of an endoscope shaft. Thus, the term "jacket tube" in this patent application refers to this function and not necessarily to the position as outermost, enveloping tube of the endoscope shaft.

The sensor module carrier is preferably designed as a rigid signal line carrier or as an inner tube. Corresponding rigid signal line carriers or signal conductor carriers are shown for example in the patent applications DE 10 2010 044 786.2 and DE 10 2011 076 077.6 of the applicant, the disclosure content of which shall be fully incorporated into the present patent invention by reference. This includes an insulating conductor carrier, on or in which signal lines or respectively conductor paths are arranged. The rigid signal line carrier is in particular cylindrical and longitudinally extending and can be produced for example in casting or injection-molding technology. The application of the conductor paths takes place for example in the technology of the production of Molded Interconnection Devices. Alternatively, a rigid signal line carrier can also be designed as a rigid flat conductor path carrier. Alternatively, the sensor module carrier is designed as an inner tube, which is rotatably mounted concentrically in the jacket tube. The jacket tube can also have for example signal conductors on its inside or on its outside.

The sensor module carrier and/or the sensor module is preferably rotatably mounted with respect to the jacket tube via two slide bearings, wherein in particular a proximally arranged slide bearing has a fluid seal and/or is designed in a water-tight manner. The sensor module carrier and the sensor module are rotatably mounted in the jacket tube by the two slide bearings. The sensor module carrier and the sensor module are simultaneously secured from tipping in the jacket tube.

In order to avoid penetration of steam into the endoscope and the precipitation of condensation on the glasses of the prism and the sensor module, a fluid seal is preferably provided. This type of fluid seal can be designed as a magnetic ferrofluidic seal. Such a magnetic ferrofluidic seal comprises a ring magnet, which is arranged around the part to be sealed, for example the sensor module carrier, and leaves open a gap to the sensor module carrier. A ferrofluid is arranged in the gap, which consists of a suspension of nanoparticles made of ferromagnetic material. The nanoparticles have a diameter that is less than a magnetic domain. In this case, the suspension medium is preferably an oil. The small size of the nanoparticles causes them to be subject to the Brownian molecular motion in the suspension medium and to not attach to each other. An agglomeration of the nanoparticles can also be prevented in that a corresponding coating is applied to the nanoparticles.

The nanoparticles are aligned in the magnetic field of the ring magnet accordingly so that the ferrofluid fills up the entire gap. The magnetic field also holds this ferrofluid in this gap so that it does not reach the outside. Several fluid seals or respectively a cascade of several annular openings with corresponding ferrofluid can also be provided on the ring magnet in order to increase the resistance with respect to the ambient air pressure or water vapor pressure.

Finally, the proximal slide bearing can also be designed water-tight in order to prevent the penetration of liquid water during autoclaving.

The corresponding locking means are preferably designed in cross-section essentially in a form-locked and/or force-locked manner, in particular as tongue and groove or as groove and spring-preloaded spring. The form lock and/or force lock of the corresponding locking means prevents any wobbling of the attachment or respectively carrier against the jacket tube in the circumferential direction. The groove can thereby be provided on the attachment and the corresponding complementary shape in the jacket tube or vice versa.

The locking means advantageously extends on the jacket tube over a part of the longitudinal extension of the jacket tube. It is thereby possible during the pushing of the attachment applied to the sensor module into the jacket tube to capture early on the orientation of the prism or mirror with respect to the jacket tube and to retain this orientation during the entire pushing in action. In particular, in such a case, the attachment can already be threaded on the proximal end of the jacket tube with its locking means on the locking means in the jacket tube, which spares a subsequent rotation near the distal end of the endoscope shaft.

A slide bearing is preferably arranged between the sensor module and the attachment. The attachment and the sensor module are thus mounted on each other directly, which results in a space-saving construction.

The attachment is furthermore preferably designed to receive the sensor module and the slide bearing on its proximal side, wherein a retention structure for a form-locking and/or force-locking coupling with a corresponding structure of the sensor module or of the sensor module carrier is provided on a proximal edge for holding the sensor module in the axial direction. This can take place in the form of an edge, which is also designed in the axial direction with tongue or groove, wherein the sensor module or the sensor module carrier has the corresponding tongue or groove in an area of the distal end on its perimeter, so that in turn a tongue and groove connection between the sensor module or sensor module carrier and attachment is realized. The connection permits the axial twisting of the two components against each other. An axial pulling apart is thereby prevented at least up to a predetermined or predeterminable expenditure of force.

The object underlying the invention is also solved through a method for mounting a previously described video endoscope according to the invention, wherein an entry window is hermetically connected with the jacket tube and furthermore a slide-in group is established by connecting the sensor module in a rotationally fixed manner with the sensor module carrier and connecting the attachment rotatably with the sensor module, wherein the slide-in group is inserted into the jacket tube, wherein during the pushing in the at least one locking means engages on the attachment with the at least one locking means on the jacket tube.

The formation of the slide-in group on one side and the distal hermetic sealing of the jacket tube on the other side makes it possible to clean the jacket tube or respectively the entry window from the inside before the slide-in group is pushed into the jacket tube. At the same time, the slide-in group and in particular the distally arranged prism or mirror are not near the location where the sealing takes place during the hermetic sealing of the jacket tube so that the prism or the mirror is also not dirtied during this process.

The entry window and/or the jacket tube are preferably freed of impurities from the hermetic connection of the entry window with the jacket tube before the slide-in group is pushed into the jacket tube. A meniscus lens is also preferably mounted on a distal end face of the prism or of the mirror before the pushing in of the slide-in group. This can occur before or after the prism or the mirror is installed in the attachment or after the attachment with the prism or mirror has been pushed onto the sensor module.

The optics of the attachment and/or the optics of the sensor module is advantageously focused before the slide-in group is pushed into the jacket tube and before and/or after the attachment is connected with the sensor module. This means that the individual optical components, for example the meniscus lens, the prism, the mirror and other lenses are aligned with respect to each other in the optical path in front of the sensor in order to obtain a desired sharp image in the desired viewing direction.

The sideways viewing direction of the video endoscope according to the invention is either permanently preset or is adjustable in stages or in a continuously variable manner. Corresponding mechanisms or solutions with actuators or mechanical means are known and can also be implemented with the mounting concept shown in the present invention.

Further characteristics of the invention will become apparent from the description of the embodiments according to the invention together with the claims and the included drawings. Embodiments according to the invention can fulfill individual characteristics or a combination of several characteristics.

BRIEF DESCRIPTION OF THE DRAWING

The invention is described below, without restricting the general idea of the invention, based on an exemplary embodiment with reference to the drawing, whereby we expressly refer to the drawing with regard to the disclosure of all details according to the invention that are not explained in greater detail in the text.

FIG. 2 is a magnified view of endoscope shaft 2 and the proximal area of the signal line carrier 31. In this embodiment, the slide bearing with fluid seal 32 includes fluid seal 33 between the slide bearing with fluid seal 32 and jacket tube 3.

FIG. 3 is a magnified view of endoscope shaft 2 and the proximal area of the signal line carrier 31. In this embodiment, the slide bearing with fluid seal 32 includes a watertight coating between the slide bearing with fluid seal 32 and jacket tube 3.

FIG. 4 is a magnified view of the jacket tube 3 and the groove 5. In this embodiment, springs are included between the catch 15 and the prism holder 13.

FIG. 5 is a magnified view of the jacket tube 3 and the groove 5. In this embodiment, a tongue 35 extends from the prism holder 13 into the groove 5.

DETAILED DESCRIPTION

Figure 1:
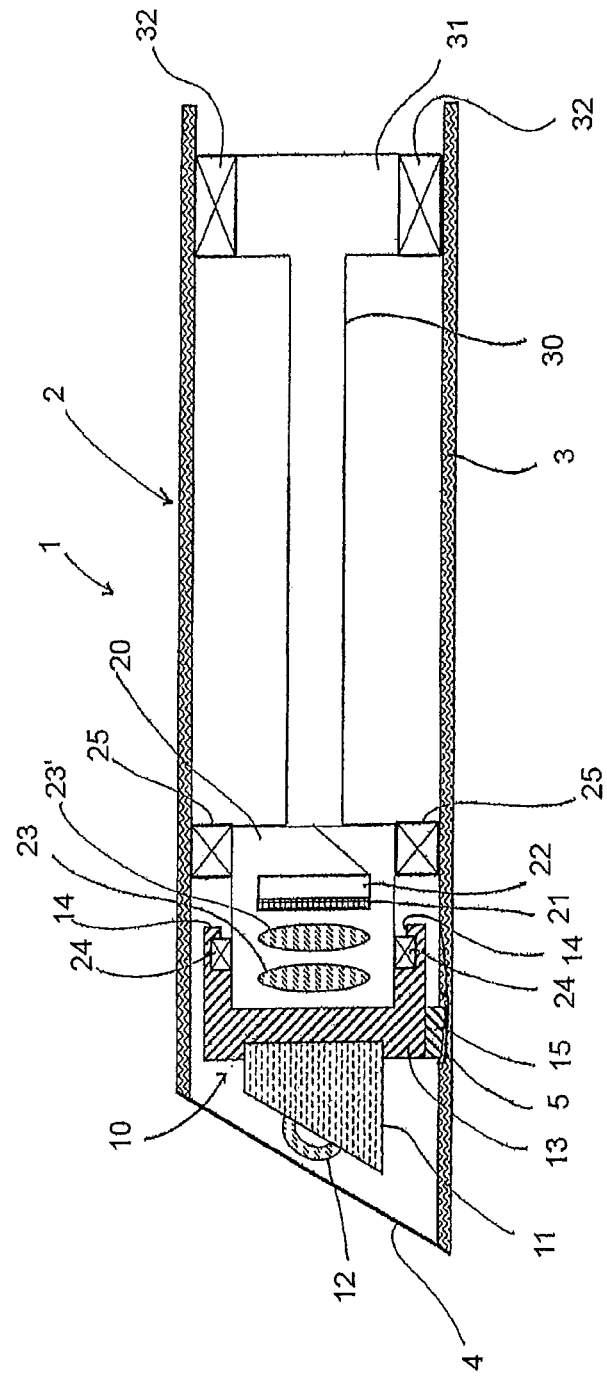
FIG. 1 shows an exemplary embodiment of a video endoscope 1 schematically in cross-section with a longitudinally extended endoscope shaft 2. A proximally arranged handle is not shown for the sake of clarity.

The endoscope shaft 2 comprises a jacket tube 3, which is closed on its distal tip by a planar entry window 4, which is soldered circumferentially with the jacket tube 3 so that a hermetic seal is achieved. Water and water vapor thus cannot get into the jacket tube 3 from the distal side during autoclaving and damage the optical components, which are arranged inside the jacket tube 3. The jacket tube 3 can in turn be surrounded by tubes or layers not shown in the FIGURE.

These optical components are combined into a slide-in group. Distally, it comprises an attachment 10 with a prism 11, on which a meniscus lens 12 is arranged. The prism 11 deflects laterally incident beams of light in an axial direction. The prism 11 is held by a prism holder 13, which is mounted on a sensor module 20. The sensor module 20 includes an optical sensor 21 on a sensor carrier 22 as well as lenses 23, 23' located in front of the sensor 21, which map or focus the light deflected by the prism 11 to the sensor 21.

The connection between the prism holder 13 and the sensor module 20 is essentially a plug connection. This plug connection permits an axial rotation of the prism holder 13 with respect to the sensor module 20 and vice versa. This is achieved through a slide bearing 24 arranged between the two components. In order to prevent an axial decoupling, the prism holder 13 has an overhang 14 or projection on its perimeter on its proximal end, which has an inward pointing edge on its proximal end. The slide bearing 24, which is connected with the sensor module 20, is received in the annular hollow space formed in this manner during the sticking together of the sensor module 20 and the prism holder 13. Alternatively, the slide bearing 24 can also be connected with the prism holder 13 and a separate circumferential structure can be present on the sensor module 20, with which the edge or respectively the overhang 14 of the prism holder 13 can be actively connected.

In order to be able to change the sideways viewing direction, the outer jacket tube 3 is rotated in the case of the endoscope according to the invention according to the FIGURE. For this purpose, the prism 11 is connected with the prism holder 13 of the attachment 10 via a catch 15 with the jacket tube 3. For this, the jacket tube 3 has a groove 5, into which the catch 15 engages. The catch 15 can be a so-called spring, i.e. an engagement body for the groove, which can also be spring-preloaded. When the catch 15 is inserted into the groove 5 of the jacket tube 3, any rotation around the longitudinal axis of the prism holder 13 and thus of the prism 11 is blocked with respect to the jacket tube 3 and the planar entry window 4 so that any rotation of the jacket tube 3 is also transferred to the prism 11.

The sensor module 20 is rotatably mounted with respect to the jacket tube 3. For this, a slide bearing 25 is provided in the distal area of the endoscope shaft 2, which is arranged between the jacket tube 3 and the sensor module 20. Another slide bearing 32 is arranged in the proximal area of the endoscope shaft 2 and rotatably mounts a proximal part of the sensor module carrier 30 with respect to the jacket tube 3. A tipping of the slide-in group out of the attachment 10, sensor module 20 and sensor module carrier 30 with respect to the jacket tube 3 is thereby prevented.

The sensor module carrier is designed in the exemplary embodiment according to the FIGURE as a longitudinally extended, rigid signal conductor carrier, the proximal area 31 of which is extended. Not shown are signal conductor paths on the surface or inside the rigid signal conductor carrier. The signal conductor carrier corresponds for example to a signal conductor carrier as is known from the patent applications DE 10 2010 044 786.2 or DE 10 2011 076 077.6 of the applicant.

The slide bearing 32 comprises in particular a fluid seal, for example a magnetic ferrofluid seal, which hermetically seals the inside of the jacket tube 3 distally of the slide bearing 32 and prevents a penetration of water vapor during the autoclaving of the endoscope 1. The slide bearing 32 can also be designed in a water-tight manner such that additionally liquid water cannot penetrate either or respectively the fluid seal is protected from liquid water.

Instead of a rigid signal conductor carrier 30, as is shown in the FIGURE, for example a rigid conductor plate or an inner tube can also be used, in which the sensor module 20 is distally arranged and that is also rotatably mounted by means of slide bearings 25, 32 with respect to the jacket tube 3. The attachment 10 can then also be mounted on the inner tube, which surrounds the sensor module 20.

In contrast to the exemplary embodiment in the FIGURE, it is also possible to design the groove 5 in the jacket tube 3 over the entire length of the jacket tube 3 or over a large part of the length of the jacket tube 3 so that the catch 15 can be threaded into the groove 5 already during the pushing in of the slide-in group 10, 20, 30 and thus the orientation of the attachment 10 is already determined at the start of the slide-in. This facilitates the mounting of the endoscope 1 according to the invention.

Instead of a fixed prism, a video endoscope according to the invention can also have a continuously variable viewing direction or a viewing direction that is adjustable in stages. Corresponding control means, e.g. actuators or mechanical transmitters of control movements, can communicate with the attachment or can themselves be arranged on the attachment.

All named characteristics, including those taken from the drawing alone, and individual characteristics, which are disclosed in combination with other characteristics, are considered alone and in combination as important to the invention. Embodiments according to the invention can be fulfilled through individual characteristics or a combination of several characteristics.

LIST OF REFERENCES

1 Video endoscope
2 Endoscope shaft
3 Jacket tube
4 Planar entry window
5 Groove
10 Attachment
11 Prism
12 Meniscus lens
13 Prism holder
14 Overhang
15 Catch
20 Sensor module
21 Optical sensor
22 Sensor carrier
23, 23' Lenses
24 Slide bearing
25 Slide bearing
30 Sensor module carrier
31 Proximal area of the signal line carrier
32 Slide bearing with fluid seal

What is claimed is:

1. A video endoscope with a sideways viewing direction, the video endoscope comprising:
   an endoscope shaft having a jacket tube;
   an entry window joined hermetically to the jacket tube at a distal end of the jacket tube;
   a sideways viewing optical subassembly including a sensor module, the sensor module having an optical sensor, the sensor module being disposed on a distal side of a longitudinally extended sensor module carrier that is rotatably mounted with respect to the jacket tube;
   wherein the sideways viewing optical subassembly is configured as an attachment, which can be or is plugged distally onto the sensor module and/or the sensor module carrier and which is rotatably mounted with respect to the sensor module and/or the sensor module carrier; and
   the attachment includes at least one locking means which interacts with at least one corresponding locking means on the jacket tube such that the attachment is rotationally fixed with respect to the jacket tub,
   wherein the sensor module carrier is configured as one of a rigid signal line carrier or as an inner tube, and wherein
   at least one of the sensor module carrier and the sensor module is rotatably mounted with respect to the jacket tube via two slide bearings, one of which is arranged proximally relative to the other, wherein the proximally arranged slide bearing has at least one of a fluid seal or is configured in a water-tight manner.

2. The video endoscope according to claim 1, wherein the at least one locking means and at least one corresponding locking means are configured in cross-section essentially in one or more of a form-locking and/or force-locking manner.

3. The video endoscope according to claim 2, wherein the at least one locking means and at least one corresponding locking means are configured as a tongue and groove or a groove and spring-preloaded spring.

4. The video endoscope according to claim 1, wherein the locking means on the jacket tube extends over a part of a longitudinal extension of the jacket tube.

5. The video endoscope according to claim 1, wherein one of the two slide bearings is arranged between the sensor module and the attachment.

6. The video endoscope according to claim 5, wherein the attachment is configured to receive the sensor module and the one of the two slide bearings on its proximal side, further comprising a retention structure for one or more of a form-locking and force-locking coupling with a corresponding structure of the sensor module or of the sensor module carrier on a proximal edge for holding the sensor module in an axial direction.

7. The video endoscope according to claim 1, wherein the entry window is disposed obliquely with respect to a longitudinal axis of the jacket tube.

8. A method for mounting a video endoscope, the endoscope comprising:
   an endoscope shaft having a jacket tube;
   an entry window joined hermetically to the jacket tube at a distal end of the jacket tube;
   a sideways viewing optical subassembly including a sensor module, the sensor module having an optical sensor, the sensor module being disposed on a distal side of a longitudinally extended sensor module carrier that is rotatably mounted with respect to the jacket tube;
   wherein the sideways viewing optical subassembly is configured as an attachment, which can be or is plugged distally onto the sensor module and/or the sensor module carrier and which is rotatably mounted with respect to the sensor module and/or the sensor module carrier; and
   the attachment includes at least one locking means which interacts with at least one corresponding locking means on the jacket tube such that the attachment is rotationally fixed with respect to the jacket tube,
   wherein the sensor module carrier is configured as one of a rigid signal line carrier or as an inner tube, and wherein at least one of the sensor module carrier and the sensor module is rotatably mounted with respect to the jacket tube via two slide bearings, one of which is arranged proximally relative to the other, wherein the proximally arranged slide bearing has at least one of a fluid seal or is configured in a water-tight manner,
   the method comprising:
   hermetically connecting an entry window with the jacket tube and furthermore establishing a slide-in group by connecting the sensor module in a rotationally fixed manner with the sensor module carrier and connecting the attachment rotatably with the sensor module, wherein the slide-in group is inserted into the jacket tube, wherein the at least one locking means on the attachment engages with the at least one locking means on the jacket tube during the pushing in.

9. The method according to claim 8, wherein the entry window and/or the jacket tube are freed of impurities from the hermetic connection of the entry window with the jacket tube before the slide-in group is pushed into the jacket tube.

10. The method according to claim 8, characterized in that an optics of the attachment and/or an optics of the sensor module is focused before the slide-in group is pushed into the jacket tube and before and/or after attachment is connected with the sensor module.

* * * * *